United States Patent
Savord

(10) Patent No.: US 12,257,107 B2
(45) Date of Patent: Mar. 25, 2025

(54) ULTRASOUND TRANSDUCER PROBE BASED ANALOG TO DIGITAL CONVERSION FOR CONTINUOUS WAVE DOPPLER, AND ASSOCIATED DEVICES, SYSTEMS, AND METHODS

(71) Applicant: KONINKLIJKE PHILIPS N.V., Eindhoven (NL)

(72) Inventor: Bernard Joseph Savord, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 124 days.

(21) Appl. No.: 18/010,018

(22) PCT Filed: Jun. 16, 2021

(86) PCT No.: PCT/EP2021/066166
§ 371 (c)(1),
(2) Date: Dec. 13, 2022

(87) PCT Pub. No.: WO2021/259714
PCT Pub. Date: Dec. 30, 2021

(65) Prior Publication Data
US 2023/0225707 A1    Jul. 20, 2023

Related U.S. Application Data

(60) Provisional application No. 63/042,601, filed on Jun. 23, 2020.

(51) Int. Cl.
*A61B 8/00* (2006.01)
*A61B 8/06* (2006.01)
*A61B 8/08* (2006.01)

(52) U.S. Cl.
CPC .............. *A61B 8/4488* (2013.01); *A61B 8/06* (2013.01); *A61B 8/463* (2013.01); *A61B 8/488* (2013.01)

(58) Field of Classification Search
CPC ......... A61B 8/4488; A61B 8/06; A61B 8/463; A61B 8/488
See application file for complete search history.

(56) References Cited

U.S. PATENT DOCUMENTS 4,015,262 A     3/1977   Etcheverry et al.
2002/0061738 A1  5/2002   Simmons et al.
(Continued)

FOREIGN PATENT DOCUMENTS

CN    108111170 A     6/2018
DE    102005026928 A1  2/2006
(Continued)

OTHER PUBLICATIONS

International Search Report and Written Opinion for PCT/EP2021/066166; Mailing date: Sep. 8, 2021, 11 pages.

*Primary Examiner* — Chao Sheng

(57) ABSTRACT

An ultrasound system includes a transducer array configured to generate analog ultrasound signals. The system includes one or more analog-to-digital converters (ADCs) in communication with the transducer array. The ADCs is configured to convert the analog ultrasound signals to digital ultrasound signals. The system includes a processor circuit in communication with the ADCs. The processor circuit includes digital in-phase/quadrature (I/Q) mixers configured to generate digital continuous wave (CW) Doppler signals based on the digital ultrasound signals. The processor circuit is configured to process the digital CW Doppler signals, generate a graphical representation of a distribution of blood flow velocities over a plurality of cardiac cycles, and output (Continued)

the graphical representation to a display in communication with the processor circuit.

14 Claims, 10 Drawing Sheets

(56) References Cited

U.S. PATENT DOCUMENTS

| | | |
|---|---|---|
| 2003/0091125 A1 | 5/2003 | Glas et al. |
| 2005/0068221 A1 | 3/2005 | Freeman et al. |
| 2006/0241464 A1 | 10/2006 | Ohtake et al. |
| 2007/0239001 A1* | 10/2007 | Mehi .................. G10K 11/346 600/437 |
| 2008/0188747 A1* | 8/2008 | Randall ............... G01S 7/52073 600/443 |
| 2011/0245677 A1* | 10/2011 | Sato .................... G01S 7/52079 600/447 |
| 2019/0227165 A1 | 7/2019 | Savord et al. |
| 2021/0007717 A1 | 1/2021 | Savord |

FOREIGN PATENT DOCUMENTS

| | | | |
|---|---|---|---|
| KR | 20170059672 A | * | 5/2017 |
| WO | 2015076439 A1 | | 5/2015 |

* cited by examiner

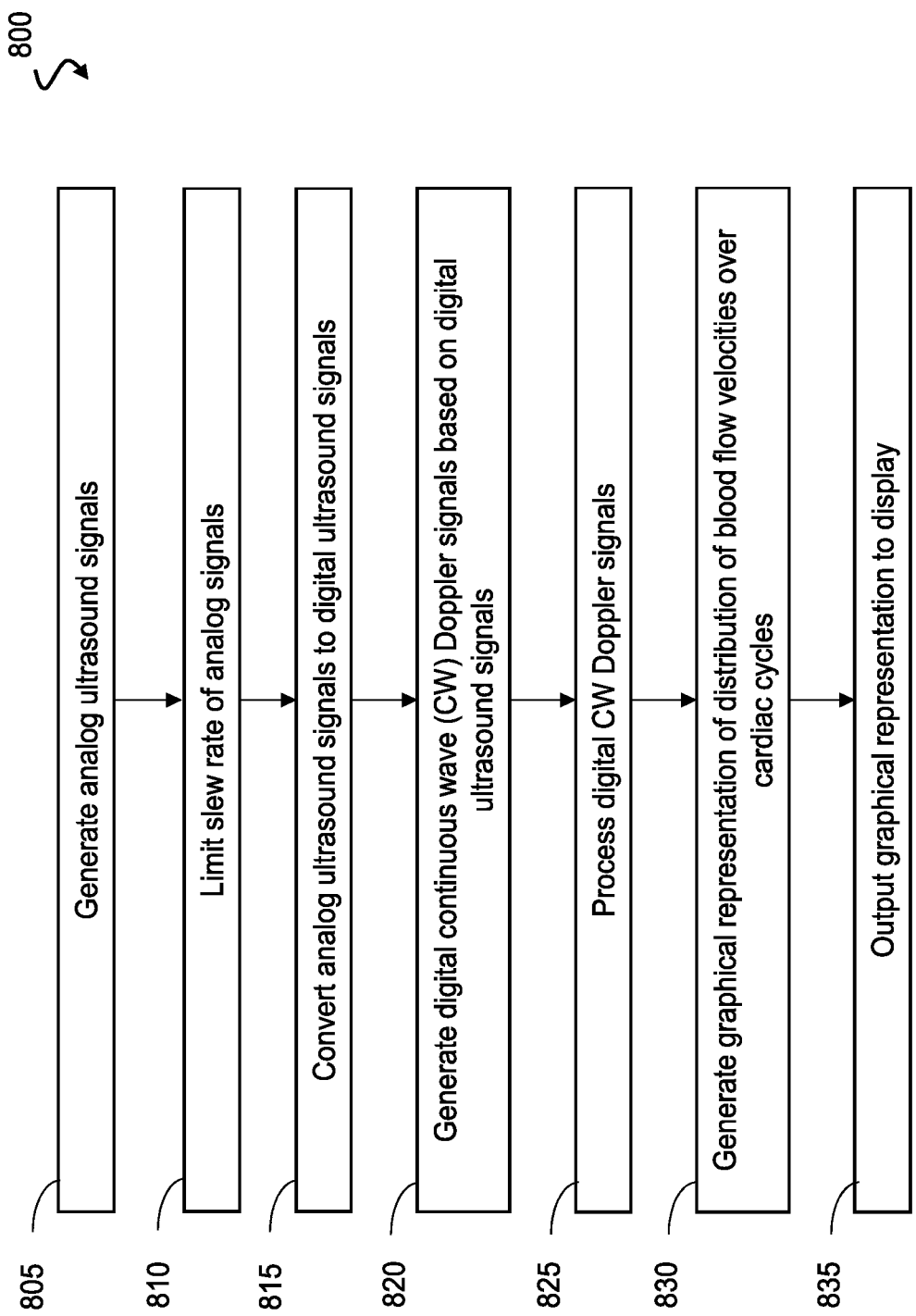

ULTRASOUND TRANSDUCER PROBE BASED ANALOG TO DIGITAL CONVERSION FOR CONTINUOUS WAVE DOPPLER, AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2021/066166, filed on Jun. 16, 2021, which claims the benefit of U.S. Provisional Patent Application No. 63/042,601, filed on Jun. 23, 2020. These applications are hereby incorporated by reference herein.

TECHNICAL FIELD

The present disclosure relates generally to ultrasound imaging, such as continuous wave (CW) Doppler imaging. In particular, analog CW Doppler signals are converted to digital signals at the transducer probe and transmitted to a host system over a low-cost, high-speed, digital multi-lane communication link.

BACKGROUND

Ultrasound imaging systems are widely used for medical imaging. An ultrasound imaging system typically includes a transducer probe separate from a main processing system. The transducer probe has an array of ultrasound transducer elements. The ultrasound transducer elements send acoustic waves through a patient's body and generate signals as the acoustic waves are reflected back by the tissues and/or organs within the patient's body. In traditional ultrasound applications, the timing and/or strength of the echo signals may correspond to the size, shape, and mass of the tissues, organs, or other features of the patient and images depicting the measured tissues, organs, or other features may be displayed to a user of the ultrasound system. Some ultrasound applications additionally employ continuous wave (CW) Doppler imaging methods to measure velocities within the patient's body, such as movement of liquid (e.g., blood flow). Typically, raw analog ultrasound echo signals corresponding to each transducer element are passed through a cable from the transducer probe to the main processing system for processing. For B-mode applications, the processing system processes the analog ultrasound signal by first digitizing them with analog to digital convertors and then further processing them using digital techniques and generates ultrasound images depicting tissues and/or organs within the patient. In CW Doppler applications, the processing system processes the analog ultrasound signal using analog mixers and filters to combine element data prior to digitization. Further processing of the digitized signal generates a graphical representation of velocities within the patient over time.

To transmit raw analog ultrasound echo signals from the probe to the main processing system, the connecting cable usually has many conductors, and in some instances, may require a conductor or set of conductors for each receiving ultrasound transducer element, making it thick, complex, cumbersome, and unwieldy. The size or diameter of the cable may also be large as the cable is required to carry received echo signals from each ultrasound transducer element to the main processing system. As a result, the cost of the cable can be the costliest component in an ultrasound imaging system. The cable may also have a high failure rate.

One approach to overcoming the limitations of analog processing is to include low-power analog-to-digital converters (ADCs) in the transducer probe, perform full or partial beamforming digitally at the transducer probe, and transfer the digital signals via a reduced number of conductors to the main processing system. This method, if used in traditional ultrasound imaging systems, may significantly reduce the cost, diameter, and overall maneuverability of the cable connecting the ultrasound imaging probe and the main processing system. However, due to the high dynamic range of CW Doppler ultrasound signals, such an approach is unsuitable for CW Doppler imaging. In particular, the low-power ADCs used to convert raw analog signals to digital signals within an ultrasound imaging probe do not have sufficient dynamic range to properly receive and convert analog signals associated with CW Doppler imaging. As a result, in ultrasound imaging systems with both a B-mode ultrasound imaging path and a CW Doppler path, ultrasound imaging signals for B-mode imaging may be converted to digital signals within the probe, but the signals for CW Doppler signals cannot be. Digital signals for B-mode imaging can be transmitted to the main processing system via a reduced number of conductors, but a separate set of conductors, including one or more conductors corresponding to each receiving transducer element, must be retained for carrying analog signals for CW Doppler imaging in the cable, resulting in the same undesired bulk and cost of transmitting analog signals.

SUMMARY

Embodiments of the present disclosure are systems, devices, and methods for continuous wave (CW) Doppler ultrasound imaging. An ultrasound system includes a host, a probe, and a connecting cable between the host and the probe. The ultrasound imaging probe includes an array of ultrasound transducers that transmit ultrasound signals toward an anatomy and receive waves reflected from the anatomy. The received ultrasound waves may be used for CW Doppler imaging of velocities within the patient's anatomy. An example of such a velocity is the velocity of blood flow, e.g., between chambers of the heart (e.g., between an atrium and a ventricle). Analog CW Doppler signals may be converted to digital signals within the ultrasound imaging probe. These digital CW Doppler signals may be combined within the probe before being transmitted to the ultrasound host via the connecting cable. Because digital data may be more easily combined, the number of conductors needed to transmit CW Doppler data may be significantly reduced by converting analog signals to digital signals within the probe. In turn, the cost of the cable may also be significantly decreased. The cable and probe may also become more easily managed and maneuvered by a sonographer. Accordingly, aspects of the present disclosure advantageously address shortcomings of existing ultrasound imaging systems.

Additional embodiments of the present disclosure include additional circuitry in the probe to convert analog CW Doppler signals to digital signals. Due to the limited dynamic range of analog-to-digital converters (ADCs), ADCs may be overdriven by the large dynamic range of analog CW Doppler signals. This results in poor data quality. Large signal slew rates result in large signal differences sample to sample. Subtle tissue and transducer positional motion can shift the sample in which the large signal transition occurs resulting in bright white spike artifacts in the Doppler display. Soft limiters and low pass filters may be positioned before ADCs in the signal processing path within the probe to reduce the dynamic range and slew rate of the analog CW Doppler signals. A switch may also engage unused ADCs associated with transmit transducers into parallel communication with ADCs associated with receive transducers. This parallel configuration doubles the ADCs used to convert analog CW Doppler signals and increases the combined dynamic range of the ADCs in the probe by at least 3 dB. This increase helps to prevent the ADCs from being overdriven and preserves good signal and data quality. Reducing the dynamic range of analog CW Doppler signals, increasing the dynamic range of the ADCs in the probe, and/or converting analog CW Doppler signals to digital at the probe advantageously eliminate the need of an analog signal path for CW Doppler imaging between the probe and the host in the ultrasound imaging system.

In an exemplary aspect of the present disclosure, an ultrasound system is provided. The system includes a transducer array configured to generate analog ultrasound signals; a first analog-to-digital converter (ADC) in communication with the transducer array, wherein the first ADC is configured to convert the analog ultrasound signals to digital ultrasound signals; and a processor circuit in communication with the first ADC, wherein the processor circuit comprises digital in-phase/quadrature (I/Q) mixers configured to generate digital continuous wave (CW) Doppler signals based on the digital ultrasound signals, and wherein the processor circuit is configured to: process the digital CW Doppler signals; generate a graphical representation of a distribution of blood flow velocities over a plurality of cardiac cycles; and output the graphical representation to a display in communication with the processor circuit.

In some aspects, the system further includes analog limiter circuitry communicatively disposed between the transducer array and the first ADC. In some aspects, the analog limiter circuitry comprises soft limiter circuitry. In some aspects, the system further includes a low pass filter communicatively disposed between the analog limiter circuitry and the first ADC. In some aspects, the system further includes analog gain compression circuitry communicatively disposed between the transducer array and the first ADC. In some aspects, the system further includes a second ADC, the transducer array comprises a first acoustic element and a second acoustic element, and the first ADC is associated with the first acoustic element and the second ADC is associated with the second acoustic element. In some aspects, the system further includes a switch configured to establish communication selectively between the second ADC and the first acoustic element or the second acoustic element, and the switch establishes communication between the second ADC and the first acoustic element when the second acoustic element is a transmit element and the first acoustic element is a receive element. In some aspects, the processor circuit further includes a digital low pass filter communicatively disposed between the digital I/Q mixers and the display, and a digital high pass filter communicatively disposed between the digital low pass filter and the display. In some aspects, the system further includes an ultrasound probe comprising a housing and a cable configured to transmit the digital ultrasound signals; and a host system in communication with the ultrasound probe via the cable, the transducer array is coupled to the housing of the ultrasound probe, the first ADC is disposed within the housing, and the processor circuit is disposed within the host system. In some aspects, the system further includes a preamplifier positioned between the transducer array and the first ADC disposed within the housing of the ultrasound probe. In some aspects, the system further includes circuitry for combining digital ultrasound signals. In some aspects, the circuitry for combining digital ultrasound signals is positioned within the housing of the ultrasound probe. In some aspects, the circuitry for combining digital ultrasound signals is positioned within the host system. In some aspects, the processor circuit is configured to: process the digital ultrasound signals, generate an ultrasound image of a heart, and output the ultrasound image to the display.

In an exemplary aspect of the present disclosure, a method is provided. The method includes generating analog ultrasound signals; converting the analog ultrasound signals to digital ultrasound signals; and generating digital continuous wave (CW) Doppler signals based on the digital ultrasound signals; processing the digital CW Doppler signals; generating a graphical representation of a distribution of blood flow velocities over a plurality of cardiac cycles; and outputting the graphical representation to a display in communication with the processor circuit.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 8 is a flow diagram of an ultrasound imaging method, according to aspects of the present disclosure.

DETAILED DESCRIPTION

Figure 1:
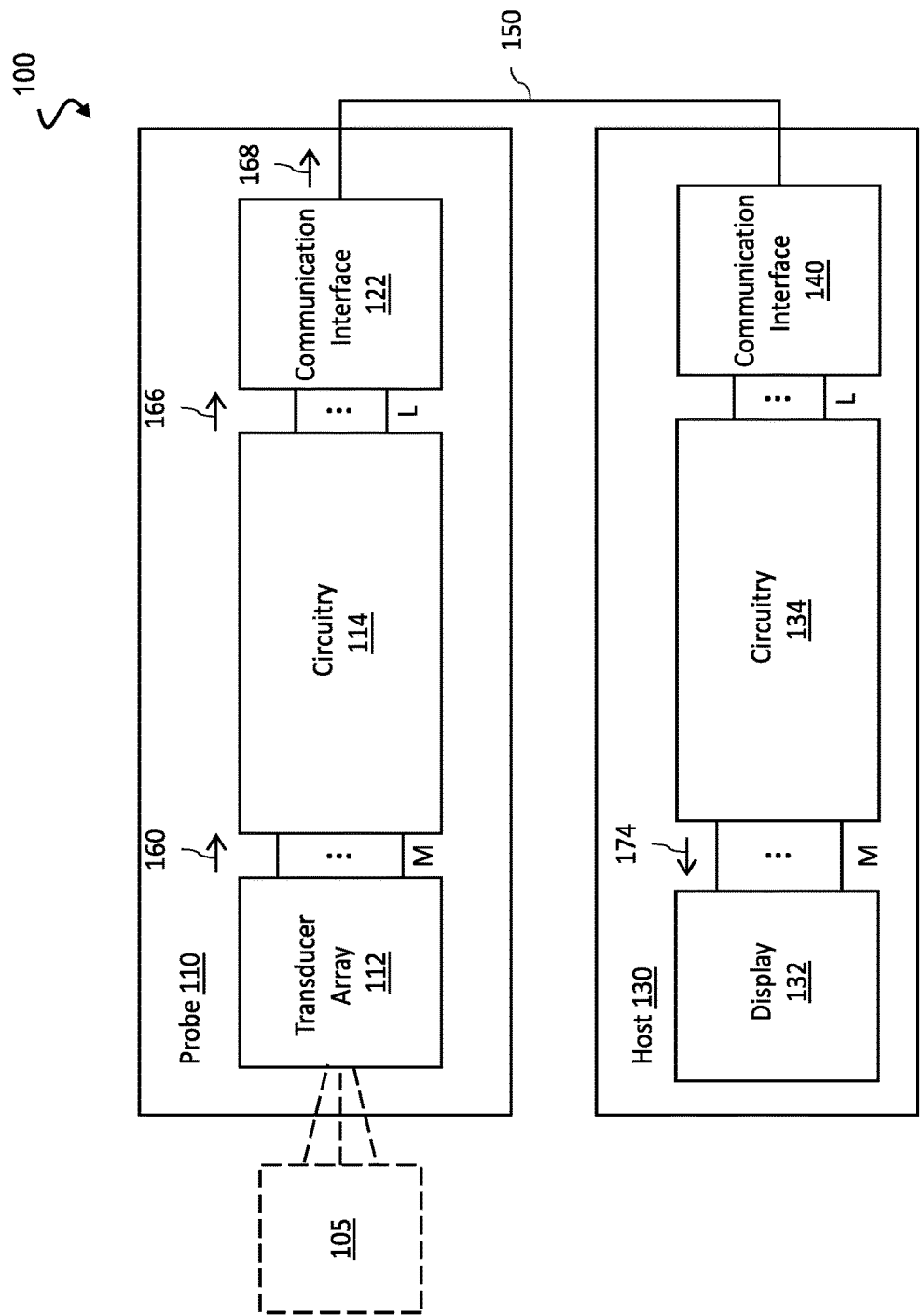
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. FIG. 1 is a schematic diagram of an ultrasound imaging system 100, according to aspects of the present disclosure. The system 100 is used for scanning a region, area, or volume of a patient's body. The system 100 includes an ultrasound imaging probe 110 in communication with a host 130 over a communication interface or link 150. At a high level, the probe 110 emits ultrasound waves towards an anatomical object 105 (e.g., a patient's body) and receives ultrasound echoes that are reflected from the object 105. The probe 110 transmits electrical signals representative of the received echoes over the link 150 to the host 130 for processing and image display. The probe 110 may be in any suitable form for imaging various body parts of a patient while positioned inside or outside of the patient's body. For example, the probe 110 may be in the form of a handheld ultrasound scanner or a patch-based ultrasound device. In some embodiments, the probe 110 can be an intra-body probe, such as a transesophageal echocardiography (TEE) probe, a catheter, or an endo-cavity probe. The probe 110 may include a transducer array 112, various circuitry 114, and a communication interface 122.

The transducer array 112 emits ultrasound signals towards the object 105 and receives echo signals reflected from the object 105 back to the transducer array 112. The transducer array 112 may include acoustic elements arranged in a one-dimensional (1D) array, 1.X dimensional array, or a two-dimensional (2D) array. The acoustic elements may be referred to as transducer elements. Each transducer element can emit ultrasound waves towards the object 105 and can receive echoes as the ultrasound waves are reflected back from the object 105. For example, the transducer array 112 can include M transducer elements producing M analog ultrasound echo signals 160. In some embodiments, M can be about 2, 16, 64, 128, 192, 1000, 5000, 9000, and/or other suitable values both larger and smaller.

Circuitry 114 positioned within the probe 110 may be any of any suitable type and may serve several functions. For example, circuitry 114 may include resistors, capacitors, transistors, inductors, relays, clocks, timers, or any other suitable electrical component that may be integrated in an integrated circuit. In addition, circuitry 114 may be configured to support analog signals and/or digital signals transmitted to or from the transducer array 112 and/or the probe 110. In some embodiments, circuitry 114 may include analog frontends (AFEs), analog-to-digital converters (ADCs), multiplexers (MUXs), and encoders, among various other components. In some embodiments, the circuitry 114 can include hardware components, software components, and/or a combination of hardware components and software components.

The communication interface 122 is coupled to the circuitry 114 via L signal lines. In some embodiments, circuitry 114 may reduce the number of required lines from M signal lines to L signal lines. This may be accomplished by any suitable method using any suitable component. For example, MUXs, beamformers, or other components may be used to reduce the M signal lines from the transducer array 112 to L signal lines 166. In the embodiment of FIG. 1, L is less than M. The communication interface 122 may be configured to transmit the L signals 166 to the host 130 via the communication link 150. The communication link 150 may include L data lanes for transferring the digital signals 168 to the host 130, as described in greater detail herein. The communication interface 122 may include hardware components, software components, or a combination of hardware components and software components. The circuit 114 and/or the communication interface 122 are configured to generate signals 168, carrying the information from the L signals 166, for transmission over the communication link 150. The signals 168 can be digital signals, analog signals, or a combination of digital signals and analog signals.

The host 130 may be any suitable computing and display device, such as a workstation, a personal computer (PC), a laptop, a tablet, a mobile phone, or a patient monitor. In some embodiments, the host 130 may be located on a moveable cart. At the host 130, the communication interface 140 may receive the digital signals 168 from the communication link 150. The communication interface 140 may include hardware components, software components, or a combination of hardware components and software components. The communication interface may be substantially similar to the communication interface 122 in the probe 110.

Circuitry 134 positioned within the host 130 may be of any suitable type and may serve any suitable function. For example, circuitry 134 may include resistors, capacitors, transistors, inductors, relays, clocks, timers, processing components, memory components, or any other suitable electrical component that may be integrated in an integrated circuit. In addition, circuitry 134 may be configured to support analog signals and/or digital signals transmitted to or from the probe 110. Circuitry 134 may be configured to process signals 168 received from the probe 110. For example, circuitry 134 may expand L signal lines received from the probe 110 to the original M signal lines corresponding to the specific transducer elements or groups/patches of transducer elements within the transducer array 112. Circuitry 134 can be configured to generate image signals 174 for display to a user and/or perform image processing and image analysis for various diagnostic modalities or ultrasound types (B-mode, CW Doppler, etc.).

Circuit 114 and/or circuitry 134 may additionally include a central processing unit (CPU), a digital signal processor (DSP), a graphical processing unit (GPU), an application-specific integrated circuit (ASIC), a controller, a field-programmable gate array (FPGA), another hardware device, a firmware device, or any combination thereof. Circuit 114 and/or circuitry 134 may also be implemented as a combination of computing devices, e.g., a combination of a DSP and a microprocessor, a GPU and a microprocessor, a plurality of microprocessors, one or more microprocessors in conjunction with a DSP core, or any other such configuration.

The display unit 132 is coupled to circuitry 134. The display unit 132 may include a monitor, a touch-screen, or any suitable display. The display unit 132 is configured to display images and/or diagnostic results processed by circuitry 134. The host 130 may further include a keyboard, a mouse, a touchscreen or any suitable user-input components configured to receive user inputs for controlling the system 100.

While FIG. 1 is described in the context of transmitting digital ultrasound echo signals from the probe 110 to the host 130 for display, the host 130 can generate signals for transmitting to the probe 110. For example, power signals, signals for controlling the probe 110 (e.g. exciting the transducer elements at the transducer array 112 to emit energy) can be transmitted by the host 130 to the probe 110 over the communication link 150.

Figure 2:
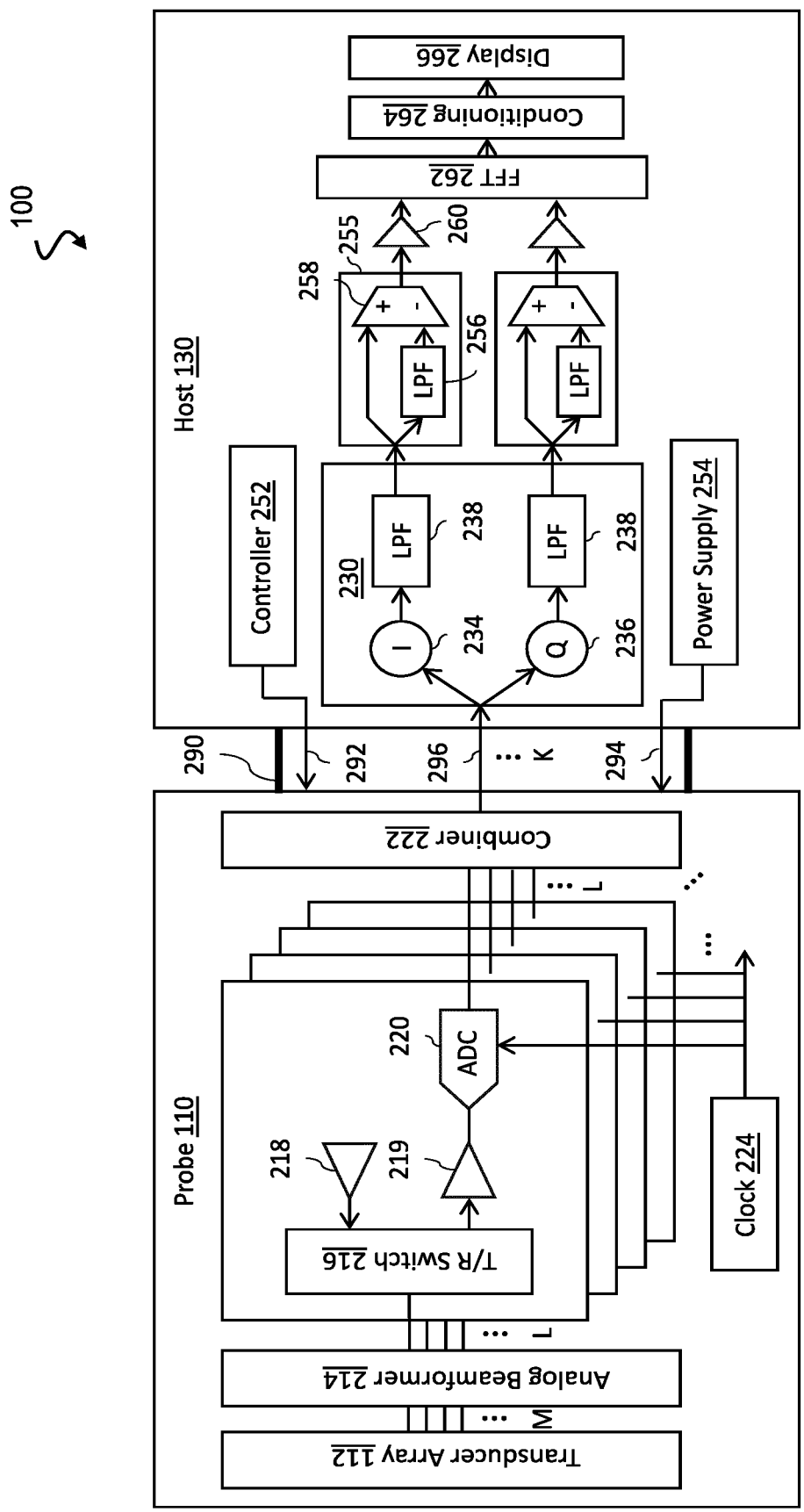
FIG. 2 is a schematic diagram illustrating example circuitry of an ultrasound imaging system, according to aspects of the present disclosure.

FIG. 2 is a schematic diagram illustrating example circuitry of an ultrasound imaging system, according to aspects of the present disclosure. FIG. 2 provides a more detailed view of the system 100 including transmission paths from the probe 110 to the host 130 and from the host 130 to the probe 110.

As shown in FIG. 2, the probe 110 further includes an optional analog beamformer 214 and L transmit receive switches (T/R switches) 216, preamplifiers 219, analog-to-digital converters (ADCs) 220, and transmit pulsers 218. The probe 110 also includes a clock 224 and combiner 222. FIG. 2 also illustrates the host 130. The host 130 may include an integrated circuit 230. The integrated circuit 230 may include in-phase/quadrature mixers 234, 236, and low pass filters (LPFs) 238. The host 130 may additionally include a controller 252, a power supply 254, a plurality of wall filters 255 (with LPFs 256 and operational amplifiers (op-amps) 258), and windowing functions 260. The host 130 may also include, among other components configured to perform various functions, or operations, a component configured to perform a fast Fourier transform (FFT) 262, a component to perform various conditioning functions 264, and a display 266. The host 130 may additionally include hardware components, software components, or a combination of hardware components and software components. As shown in FIG. 2, the probe 110 and the host 130 may be connected with multiple conductors of a connecting cable 290 establishing signal communication. These conductors may include multiple signal lines including conductors, twisted pairs, and/or any other suitable means of transferring data. For example, the connecting cable 290 can include a power conductor 294 for transmitting power from the host 130 to the probe 110. The cable 290 also includes a control signal line 292 for transmitting control and clock signals from the host 130 to the probe. The cable 290 can also include K signal lines 296 for transmitting signals from the probe 110 to the host 130.

The signal path from the probe 110 to the host 130 may begin at the transducer array 112 shown in FIG. 2. The transducer array 112 may include M transducer elements. As previously stated, in some embodiments, M can be any suitable number and the transducer elements may be of any suitable type and in any suitable arrangement. The transducer array 112 generates analog electrical signals representative of ultrasound echoes received at one or more transducer elements for any suitable imaging type (e.g., B-mode imaging, CW Doppler imaging, etc.). For CW Doppler imaging, one or more elements of the transducer array 112 are continuously emitting ultrasound energy simultaneously as one or more other elements of the transducer array 112 are continuously receiving ultrasound echoes (based on the emitted ultrasound energy). For example, half of the acoustic elements in the transducer array 112 can be transmitting while half of the acoustic elements in the transducer array 112 can be receiving. The transducer array 112 generates analog electrical CW Doppler data based on the ultrasound echoes received by the transducer elements in receive mode. In some embodiments, equal portions of the transducer array 112 operate in transmit mode and in receive mode for CW Doppler imaging.

The transducer array 112 may be in communication with an analog beamformer 214 via M signal lines. In some embodiments, the transducer array 112 may include many transducer elements. An analog beamformer 214 may be used to reduce the quantity of signal lines from the transducer array 112. For example, in some embodiments, the analog beamformer 214 may delay and sum the signals received from the transducer array 112 to create a smaller subset. The analog beamformer 214 may be a receive beamformer and/or a transmit beamformer. In embodiments in which the analog beamformer is a transmit beamformer, the analog beamformer 214 may include or be in communication with high voltage pulse generation circuitry. In other embodiments, for example, in embodiments where the transducer array 112 is a one-dimensional array of transducer elements or the number of transducer elements is otherwise reduced, the analog beamformer 214 may not be necessary or included within the probe 110. In some embodiments where the transducer array 112 is a one-dimensional array or the number of transducer elements is otherwise reduced, the analog beamformer 214 may still be included within the probe 110.

The analog beamformer 214 may be in communication with multiple T/R switches 216 via a reduced number of signal lines (e.g. L signal lines). The probe 110 can include one T/R switch 216 for every transducer element of the array 112 or for every group/patch of transducer elements. T/R switches 216 may be configured to switch positions between different transmit and receive signal paths. For example, in a position for the transmit path, a T/R switch 216 may transmit a high voltage activation signal from the pulser 218 to one or more elements of the transducer array 112 to activate one or more transducer elements 112 to emit ultrasound energy. In receive mode, a T/R switch 216 may transmit receive signals corresponding to reflected waves received by the one or more transducer elements of the transducer array 112 to the preamplifier 219. The T/R switches 216 may be in communication with the host 130 via the data line 292 and may receive instructions regarding switching between the transmit and receive signal paths through the data line 292. The T/R switches 216 may also be in communication with the host 130 through any other suitable conductor or method.

The probe 110 may additionally include transmit pulsers 218. The transmit pulsers 218 may receive a command signal generated by the host 130. In response to the command signal, the transmit pulsers 218 generate electrical excitation pulses timed to cause the transducer array 112 to produce an acoustic transmit wave-front with any desired or specified focal characteristics.

The probe 110 may include L preamplifiers 219. The preamplifiers 219 may amplify signals from the transducer array 112 received via the T/R switches 216 to improve the quality of received signals by, for example, reducing a noise floor. In some embodiments, the number of transmit pulsers 218 may be equal to the number of preamplifiers 219 and the number of T/R switches 216. For example, each T/R switch 216 may be configured to receive data from one pulser 218 and transmit data from the transducer array 112 to one preamplifier 219.

The receive signal path can be the same for CW Doppler imaging data and other imaging data (e.g., B-mode imaging data) from the transducer array to the preamplifiers 319. At the preamplifiers 319, the receive signal path diverges within the probe 110 to include different, parallel paths for CW Doppler imaging data and other imaging data. In the signal path for other imaging data, such as B-mode imaging data, each preamplifier 219 may be in communication with an ADC 220. The ADCs 220 may be configured to convert analog ultrasound echo signals into digital ultrasound echo signals. For example, the ADCs 220 may receive analog ultrasound echo signals generated by the transducer array 112, transmitted to the preamplifiers 219 via T/R switches 216, and amplified by the preamplifiers 219 and convert them into digital ultrasound echo signals. Digital ultrasound echo signals may include digital samples representing the waveforms of corresponding analog ultrasound echo signals. The ADCs 220 may employ a successive approximation ADC architecture to provide high-performance and lower-power consumption, and thus may keep total power dissipation of the probe 110 to be within a thermal budget of the probe 110. However, any suitable ADC architecture may be used for the ADCs 220.

The clock 224 may function as a master clock in the probe 110. The clock 224 may provide a clock signal to the ADCs 220 as well as other components within the probe 110.

Each ADC 220 may be in communication with the combiner 222. The combiner 222 is representative of circuitry that can reduce the total signal lines received from the ADCs 220 and reduce the number of required signal lines for transmitting data to the host 130. The combiner 222 may reduce the number of signal lines by any suitable method. In some embodiments, the combiner 222 may include a summing node. The combiner 222, as well as any other suitable component or circuitry within the system 100 may include features similar to those described in U.S. application Ser. No. 16/329,433, titled "ULTRASOUND PROBE WITH MULTILINE DIGITAL MICROBEAMFORMER," and filed Feb. 28, 2019 and/or U.S. Provisional Application No. 62/631,549, titled "DIGITAL ULTRASOUND CABLE AND ASSOCIATED DEVICES, SYSTEMS, AND METHODS," and filed Feb. 16, 2018, both of which are hereby incorporated by reference in their entirety. In some embodiments, the combiner 222 may multiplex data received from the ADCs 220 into high-speed serial links and then send the data to the host 130 to be processed. In some embodiments, the combiner 222 may be a digital beamformer that performs a second stage of beamforming (delaying and summing of signals) after the first stage of beamforming is completed by the analog beamformer 214.

FIG. 2 additionally depicts the connecting cable 290 positioned between the probe 110 and the host 130. The cable 290 may include multiple signal lines including conductors, twisted pairs, or any other suitable means of transferring data. For example, the cable 290 may include the data line 292, power line 294, and K signal lines 296. The data line 292 may be in communication with a controller 252 within the host 130. The controller 252 transmits control signals via the data line 292 for controlling the clock 224, the ADCs 220, the T/R switches 216, the pulsers 218, the analog beamformer 214, the transducer array 112, the combiner 222 or any other component within the probe 110. In some embodiments, the data line 292 may be a twisted pair of conductors. In other embodiments, the data line 292 may be a single conductor or any other suitable signal communication conduit. In various embodiments, the command signals transmitted via the data line 292 may be analog or digital signals. When digital command signals are transmitted, the data may be transmitted via the data line 292 at any suitable bit rate, such as between 400 Mbit/s and 8 Gbit/s, including values such as 2.4 Gbit/s and/or other suitable values both larger and smaller.

The power line 294 may be in communication with a power supply 254 within the host 130 or at any other suitable location. The power line 294 may provide electrical power to various components within the probe 110. In some embodiments, the power supply 254 can provide direct current (DC) power to the probe 110 via the power line 294. In some embodiments, the power supply 254 may additionally provide power to components within the host 130.

K signal lines 296 may correspond to a reduced number of signal lines output from the combiner 222. The signal lines 296 carry digital ultrasound data for CW Doppler and B-mode imaging. In some embodiments, the signal lines 296 may include only a single signal line. In other embodiments, the signal lines 296 may include two or more signal lines. The cable 290, and any corresponding conductors enclosed within the cable 290 for the data line 292, the signal lines 296, and/or the power line 294, may be of any suitable length. For example, the cable 290 and all associated conductors may be 1 meter, 2 meters, 3 meters in length or more or any suitable length therebetween. The cable 290 can be referred to as a flexible elongate member. In some embodiments, the cable can be replaced with an optical or a wireless interface.

The host 130 may include an integrated circuit 230. The integrated circuit 230 may comprise any suitable circuitry. In some embodiments, the integrated circuit 230 may be implemented in the form of an FPGA, application specific integrated circuit (ASIC), or any other suitable type of circuit. In other embodiments, the integrated circuit 230 may be a configurable processor, NPU, accelerator card, SoC, or any other component. The integrated circuit 230 may comprise in-phase/quadrature (I/Q) mixers 234, 236 and low pass filters (LPFs) 238. The I/Q mixers 234, 236 and LPFs 238 may be digital components in that they are implemented as part of the integrated circuit 230 and operate on digital signals.

The signal lines 296 may transmit digital signal data from the combiner 222 to the integrated circuit 230. At the integrated circuit 230, signals may be transmitted to two paths corresponding to the I component of the signal associated with mixer 234 and the Q component of the signal associated with mixer 236. The I mixer 234 and the Q mixer 236 may create two signals with a phase offset. For example, the I mixer 234 may define a sequence corresponding to a digital square wave (e.g., a sequence of +1 s and −1 s, or +1 s and 0 s) and multiply the sequence with received signals. The Q mixer 236 may define a similar sequence but delayed with respect to the I sequence by one quarter period (90 degrees) and multiply the sequence with received signals. The I and Q mixers 234 and 236 may multiply respective sequences in such a way to create a phase offset between the two signal paths. For example, in some embodiments, the phase offset may be 90°. The digital square wave sequences may be a square wave of any suitable frequency. For example, in the range of, but not limited to 1 Mhz to 10 Mhz The frequency of the generated digital square wave may correspond to the sample rate of the signals received by the I and Q mixers 234 and 236. The signals transmitted from the probe 110 to the host 130 via K signal lines 296 may be of any suitable sample rate. For example, in some embodiments, the signals transmitted and mixed via the I mixer 234 and the Q mixer 236 may be in the range of, but not limited to 4 Mhz to 40 Mhz. In some embodiments, the sample rate is at least four times the Doppler frequency. The sample rate of sequences generated by the I mixer 234 and Q mixer 236 may consequently be some frequency less than the sample rate of the received signals.

After a signal is received at the host 130 and mixed by the I and Q mixers 234 and 236, the signals may then be filtered via the LPFs 238. The LPFs 238 may filter any high frequency content in the received signal such that the signal corresponds primarily to audio range content. In some embodiments, the LPFs 238 may be boxcar filters. For example, the LPFs 238 may sum or average a set number of samples within the received signal into sets. The LPFs 238 may group and sum sets of 1680 samples. In other embodiments, LPFs 238 may sum sets in the range of but not limited to 100 to 6000. In embodiments in which the LPFs 238 include boxcar filters, the resulting sample rate may be reduced by the number of samples included in a particular set. In some embodiments, therefore, the sample rate of data signals after passing through the LPFs 238 may correspond to audio frequency ranges and can be processed using standard processing components. In other embodiments, the LPFs 238 may be any suitable low pass filter, such as FIR or IR digital filters, or any other suitable low pass filter.

The host 130 may additionally include one or more wall filters 255. The wall filters 255 may be digital filters, operating on digital signal data. For example, the wall filters 255 may be circuitry within the host 130. The wall filters 255 may further include LPFs 256. The wall filters 255 may be configured to filter out low or high frequency Doppler signals corresponding to arterial walls or any other static tissue within a patient. The wall filter 255 may additionally filter high amplitude low frequency content from movement within a patient from, for example, heart beats, general patient or probe movement, or other sources. In some embodiments, the wall filter 255 may be an aggressive filter. In some embodiments, the wall filter 255 may be a 40-point, 4 term Blackman-Harris filter or any other suitable filter. The wall filters 255 may also comprise high pass filters.

After signals are processed through the wall filters 255, a windowing function 260 may be applied. The windowing function 260 may be applied by a digital multiplier or any other suitable electronic component. The windowing function 260 may apply various weights to the signal prior to additional processing. A fast Fourier transform (FFT) 262 may be applied to the signal data to create a Doppler spectrum associated with velocity of movement (e.g., blood flow) within a patient. Following the FFT 262, the data may be conditioned at conditioning 264. A graphical representation of the CW Doppler data may then output for display to a user via the display 266. It is fully contemplated that any suitable form of data processing may be applied to the signal data at this or any stage in the circuitry of the present invention. For example, the host 130 may apply additional data processing techniques to enhance the quality of the signal data, identify or emphasize various characteristics or aspects of the signal data, etc. One or more of the signal processing components within the host 130 and/or probe 110 may be implemented as hardware, software, or a combination of hardware and software.

The signal pathway in FIG. 2 within the probe 110 may be shared for B-mode data and CW Doppler data. FIG. 2 illustrates the CW Doppler signal pathway within the host 130. Some components of the CW Doppler signal pathway may be shared with the B-mode signal pathway (e.g., conditioning 264, display 266), whereas other components may be dedicated for CW Doppler processing (e.g., integrated circuit 230, wall filters 255, FFT 262). The host 130 can include signal processing circuitry for generating and displaying B-mode images based on the ultrasound data obtained by the probe 110.

Figure 3:
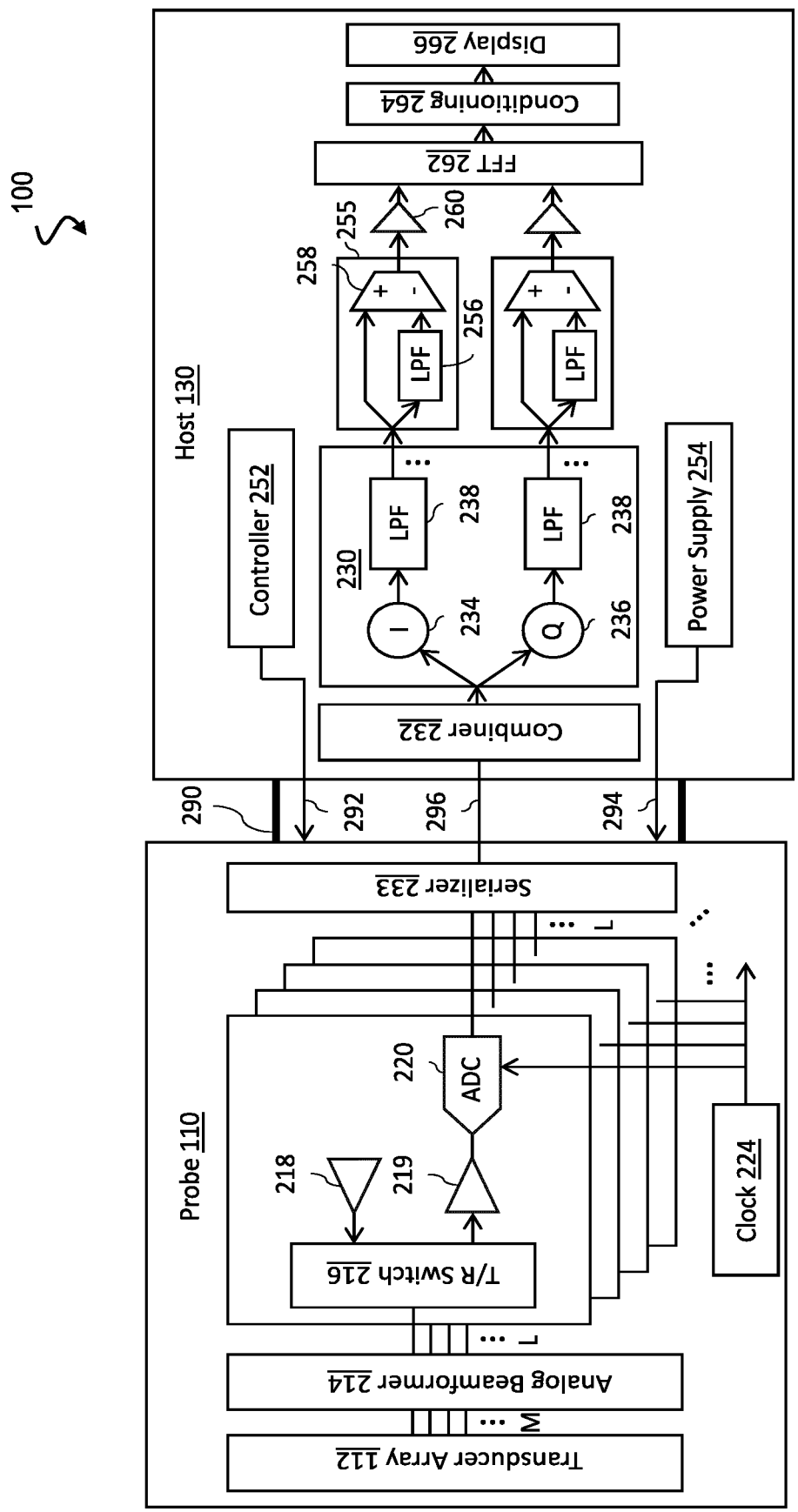
FIG. 3 is a schematic diagram illustrating example circuitry of an ultrasound imaging system, according to aspects of the present disclosure.

FIG. 3 is a schematic diagram illustrating example circuitry of an ultrasound imaging system, according to aspects of the present disclosure. FIG. 3 specifically illustrates an embodiment in which the combiner 222 is positioned within the host 130 (instead of the probe 110). In some embodiments, a serializer block 233 may be included within the probe 110 to stream the ADC data over high speed serial links to the host 130. In such an embodiment, the combiner 222 may be a digital beamformer, which performs a second stage of beamforming after the first stage of beamforming is completed by the analog beamformer 214. This embodiment may be advantageously implemented in order to simplify the signal processing circuitry within the probe 110. In this manner, the probe 110 may be better able to satisfy weight and/or thermal constraints (e.g., maximum weight and/or temperature for the probe 110), as well as to increase efficiency and reduce costs associated with manufacturing the probe 110. The serializer block 233 may additionally include a current mode logic (CML) block. The serializer block 233 may convert signals received from the ADCs 220 or any other component within the probe 110 into a bit stream for transmission to the host 130. It is also noted that the system 100 as shown in FIG. 3 and/or the probe 510 shown in FIG. 5 may additionally include a serializer block substantially similar to the serializer block 233 shown in FIG. 3.

The serializer/CML 233 may rearrange lines in communication with the combiner 232 and/or the ADC's 220 into a high rate serial data stream. In some embodiments, the serializer/CML 233 may run at a higher data rate than other circuitry within the probe 110. For example, the serial data stream may run at 160 MHz whereas other circuitry within the ultrasound signal path may run at 20 MHz. The serializer/CML 233 may operate in a similar manner to the serializer disclosed in PCT Patent Application PCT/EP2017/070804, titled "ULTRASOUND PROBE WITH MULTI-LINE DIGITAL MICROBEAMFORMER," hereby incorporated by reference in its entirety. Accordingly, in one of the signals paths of the probe 110, digital ultrasound data (e.g., B-mode data) can be transmitted from the probe 110 to the host 130 via the conductors 296. The conductors 296 may be a twisted pairs of conductors. It is understood that embodiments of the probe can include the combiner 222, the serializer 233, and/or both the combiner 22 and the serializer 233.

Figure 4:
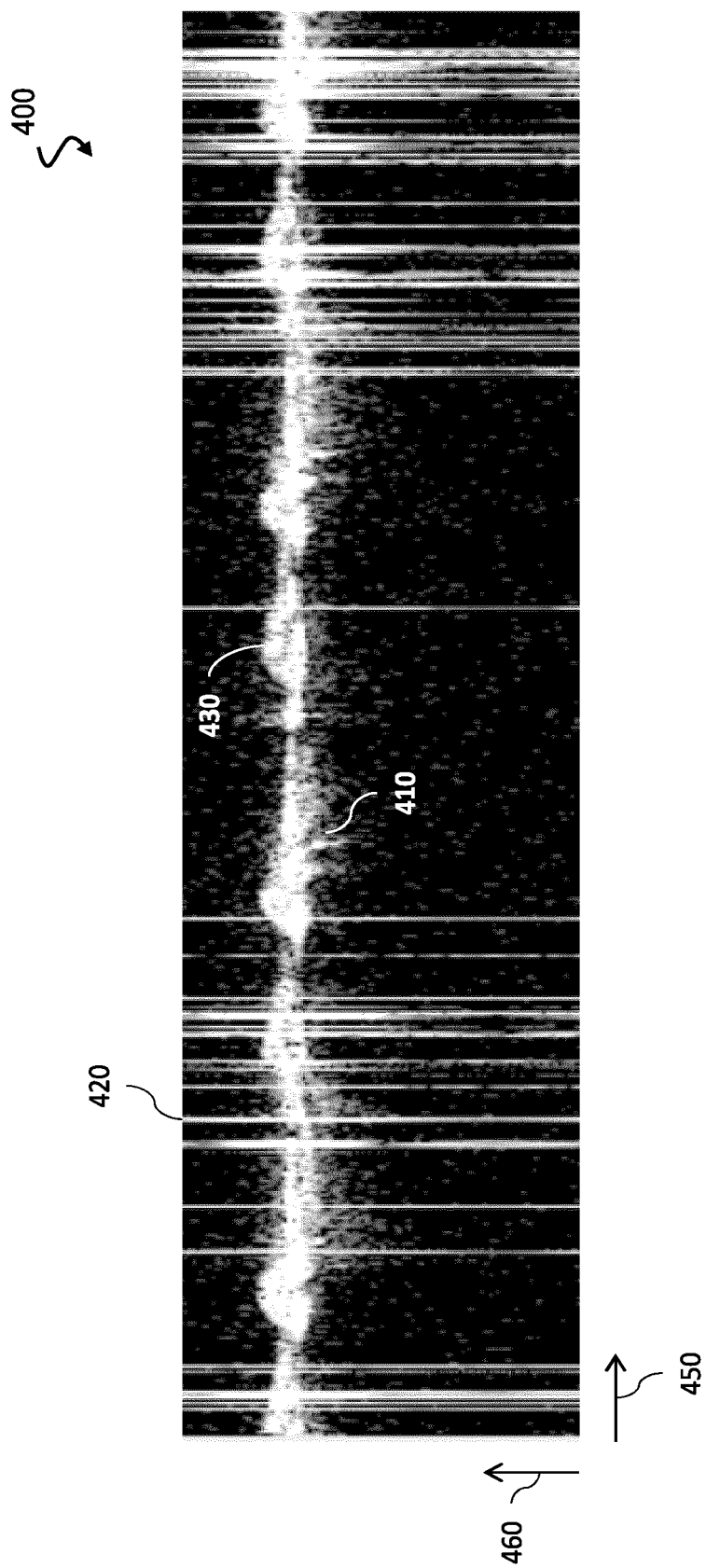
FIG. 4 is a graphical representation of a CW Doppler spectrum measured with an ultrasound imaging system, according to aspects of the present disclosure.

FIG. 4 is a graphical representation of a Doppler spectrum measured with an ultrasound imaging system, according to aspects of the present disclosure. The display 266 (FIG. 2) may display to a user a Doppler spectrum similar to the Doppler spectrum 400. The Doppler spectrum 400 may depict velocities of fluids and/or other objects within a patient. An axis in the direction 450 along the Doppler spectrum 400 may indicate a time dimension. The time dimension as illustrated in FIG. 4 by the direction 450 may be of any suitable unit. For example, the direction 450 may be measured in seconds, milliseconds, or any other suitable unit. A direction 460 along the Doppler spectrum 400 may indicate a velocity. In some embodiments, this velocity may correspond to the velocity of blood within the heart or a blood vessel of a patient. In some embodiments, the Doppler spectrum velocity may correspond to blood flow through a mitral valve within a heart. Velocity as shown along direction 460 may be measured in m/s, cm/s, mm/s, or any other suitable unit. The values 410 depicted in the Doppler spectrum 400 may indicate the velocity of a fluid at a determined location within a patient at a given time. For example, the values 410 may correspond to the velocity of blood in or around a mitral valve within a heart as it beats. Peaks 430 may correspond to moments of high velocity of blood flow. The doppler spectrum 400 may additionally depict one or more sampling errors 420. Sampling errors 420 may be caused by full scale signal transitions seen at the output of the preamplifier 219 resulting from movement by or within a patient or from thermal noise. Sampling errors 420 may be caused by large slew rate acoustic signals associated with transmit energy coupling into the receive aperture overdriving the preamplifiers 219. Such movement causing full scale signal transitions may include a heartbeat, general patient movement, probe movement, or any other sudden movements during a patient's ultrasound examination. These movements may cause a sudden change in outputs from the I mixer 234 and/or the Q mixer 236 (FIG. 2) resulting in a shift between samples and a large change in output signal. The sampling errors 420 may result from jitter on the timing of the edges of the square wave at the I and Q mixers 234 and 236. For example, sampling in the ADCs 220 will capture the signal level before the edge or after the edge depending on the instantaneous jitter. This uncertainty results in full scale sampling errors 420 which, after downstream processing, results in artefacts, or large white spikes, in the Doppler spectrum 400. As described below, aspects of the present disclosure are directed to minimizing and/or eliminating sampling errors 420 within the Doppler spectrum 400.

The Doppler spectrum 400 may be presented or depicted to a user in any suitable format. For example, the display 266 may additionally display to a user multiple metrics associated with the patient's anatomy. In some embodiments, the display 266 may include scales along any suitable direction of the Doppler spectrum 400. The display 266 may further include calculated metrics such as averages, trends, predictions, or any other suitable metric. In some embodiments, the Doppler spectrum 400 may also be referred to as a trace or spectrum trace.

Figure 5:
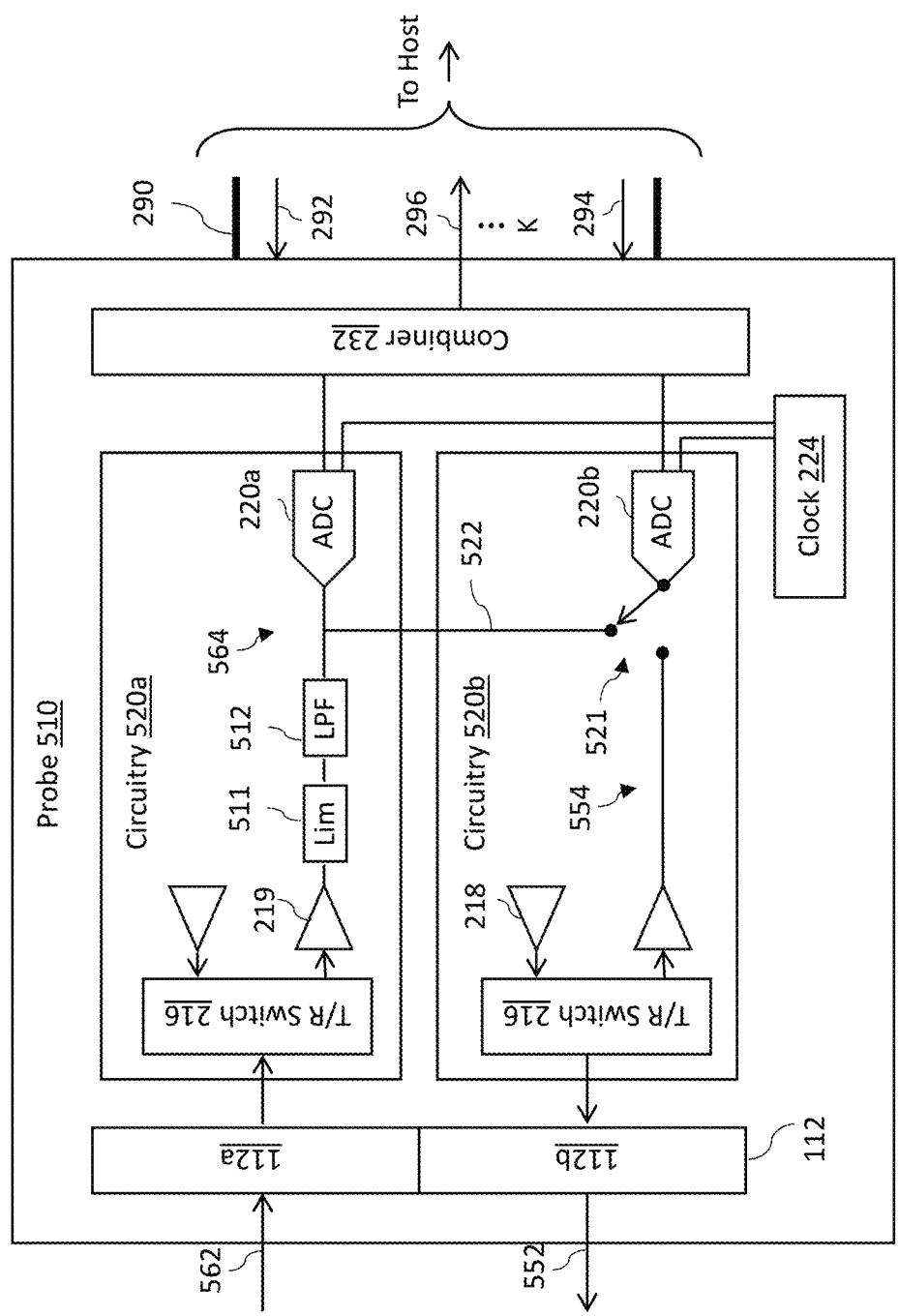
FIG. 5 is a schematic diagram illustrating example circuitry of an ultrasound imaging probe, according to aspects of the present disclosure.

FIG. 5 is a schematic diagram illustrating example circuitry of an ultrasound imaging probe, according to aspects of the present disclosure. The probe 510 illustrated in FIG. 5 may be substantially similar to the probe 110. The transducer array 112 may also include two sets of transducer/acoustic elements, a set of receiving transducers 112a and a set of transmitting transducers 112b. In some embodiments, the transducer elements may be referred to as acoustic elements. The probe 510 may include two circuitry blocks or signal paths, circuitry 520a in communication with the receiving transducer set 112a and circuitry 520b in communication with the transmitting transducer set 112b. The circuitry 520a may include a limiter 511, a low pass filter 512, and an ADC 220a. The circuitry 520b may include an ADC 220b. The circuitry 520 a may be in communication with the circuitry 520b via a connecting conductor 522 and switches 521. An ultrasound imaging system 100 capable of performing CW Doppler imaging may include multiple transducer elements within the transducer array 112 and may include multiple circuitry blocks 520a and 520b. In some embodiments, each ADC 220a and 220b may correspond to one circuitry block 520a and 520b respectively.

In CW Doppler mode, the set 112b of transducer elements (e.g., half of the transducer elements) may be used to transmit acoustic waves, illustrated by an arrow 552 in FIG. 5 the set 112a may be used to receive reflected waves, illustrated by an arrow 562.

In some embodiments, the ultrasound imaging system 100 may be capable of performing various ultrasound imaging functions in addition to CW Doppler imaging. For example, the ultrasound imaging system 100 may perform B-mode, C-mode, M-mode, power Doppler, color Doppler, shear wave, pulse inversion, and/or other imaging types. When performing other ultrasound imaging functions other than CW Doppler, the host can control one or more of the transducer elements within the transducer array 112 to selectively transmit acoustic waves illustrated by the arrow 552 and receive reflection waves illustrated by the arrow 562.

Each transducer element may be in communication with an ADC. For example, each transducer element of the receiving set 112a may be in communication with an ADC 220a. In some embodiments, multiple transducer elements may be in communication with a single ADC 220a (e.g., when an analog beamformer is provided in the probe 510 between the ADCs 220 and the transducer array 112). In such embodiments, any suitable number of transducer elements may be in communication with one ADC 220a. For example, 2, 4, 6, 8, or more transducer elements or any suitable values both larger and smaller may be in communication with an ADC 220a. Similarly, each transducer element within the transmitting set 112b may also be in communication with an ADC 220b or multiple transducer elements, including any number previously mentioned, may be in communication with a single ADC 220b. ADCs 220a may be substantially similar to ADCs 220b and both ADCs 220a and 220b may be substantially similar to ADCs 220 described herein.

The circuitry 520a may include the limiter 511. The limiter 511 may be a filter configured to limit the dynamic range of signals received by transducer elements within the receiving set 112a while maintaining good signal behavior. In some embodiments, the limiter 511 may allow signals below a specified input power or level to pass unaffected while attenuating peaks of stronger signals that exceed the threshold. In some embodiments, the limiter 511 may be a clipper, a soft clipper, a hard limiter, or any other type of suitable limiter. The limiter 511 may include analog limiter circuitry. In some embodiments, the analog limiter circuitry of the limiter 511 may include soft limiter circuitry.

The circuitry 520a may additionally include a low pass filter 512 positioned in communication with the limiter 511. The low pass filter 512 may allow signals of a frequency lower than a selected cutoff frequency and attenuate signals with frequencies higher than the cutoff frequency. The low pass filter 512 may additionally be referred to as high-cut filters in some applications. The low pass filters 512 may be of any suitable type. For example, the low pass filters 512 may be Butterworth filters, Chebyshev filters, Elliptic filters, Bessel filters, Gaussian filters, RC filters, RL filters, RLC filters, or higher order passive filters. In addition, the low pass filters 512 may include any suitable active filters and may be integrated within an integrated circuit. In some embodiments, one limiter 511 may be in communication with one low pass filter 512 as shown in FIG. 5. In other embodiments, any suitable number of limiters 511 may be in communication with one low pass filter 512 or vice versa. The combination of the limiter 511 and the low pass filter 512 may provide the ADCs 220 with slow edges that result in smaller errors in the presence of jitter or motion, as previously described.

Both the limiters 511 and the low pass filters 512 together and/or separately may serve to reduce the dynamic range of signals received by transducer elements within the receiving set of transducer elements 112a. The limiters 511 and the low pass filters 512 may also serve to reduce effects of any full scale signal transitions similar to the sampling errors 420 (FIG. 4) resulting from movement within a patient. This advantageously results in a more accurate and legible Doppler spectrum. In some embodiments, the parameters and/or specifications of the limiters 511 and/or the low pass filters 512 may reduce power consumption and thermal dissipation within the probe 510. In addition, the parameters and/or specifications of the limiters 511 and/or the low pass filters 512 may be selected and/or arranged to preserve the overall signal integrity of the signal received from transducer elements within the receiving set 112a of transducer elements while adequately reducing the dynamic range of the signal so as not to overdrive the ADCs 220a.

In some embodiments, the limiters 511 and/or the low pass filters 512 may be replaced with any suitable non-linear circuit. For example, non-linear circuits with a compression type transfer function may be used without or in combination with either the limiters 511 or the low pass filters 512. In addition, the circuitry may include analog gain compression circuitry. In some embodiments, this circuitry may be implemented via hardware. In other embodiments, this circuitry may be a software implementation.

To increase overall dynamic range of the analog to digital conversion process within the probe 510, the probe 510 may additionally include conductors 522 and switches 521. The conductors 522 may be any suitable material, shape, or size. The conductors 522 may extend from the signal path 564 of circuitry 520a to a switch 521 in communication with a signal path 554 of circuitry 520b. In some embodiments, each signal path 564 and/or circuitry 520a may correspond to one receiving transducer element and each signal path 554 and/or circuitry 520b may correspond to one transmitting transducer element. In such embodiments, the number of signal paths 564 may equal the number of signal paths 554 such that a single conductor 522 may be in communication with one signal path 564 and one signal path 554. The conductor 522 may be positioned within the probe 510 such that one end of the conductor 522 is placed in communication with the signal path 564 between an ADC 220a and a low pass filter 512. In addition, the positions of the limiter 511 and/or the low pass filter 512 need not be in the order shown in FIG. 5 but may be in any suitable order. The other end of the conductor 522 may be in communication with the signal path 554 and may be positioned at any suitable location along signal path 554. In other embodiments, the signal path 554 may additionally include limiters 511 and/or low pass filters 512 similar to signal path 564. Although only one signal path 564 and one signal path 554 are shown depicted in FIG. 5, it is understood that any suitable number of signal paths 554 and/or 564 may be included within the probe 510 such that there may be L/2 plurality of the conductors 522 within the probe 510.

As shown in FIG. 5, one end of the conductor 522 may be in communication with a switch 521. In some embodiments, while an ultrasound imaging system 100 performs imaging other than CW Doppler, the switch may be set to a position to engage the signal path 554 such that the ADC 220b may be in communication with the preamplifier 219 and the set 112b of transducer elements and is not in communication with the signal path 564 or the conductor 522. When the ultrasound imaging system 100 is to image an area of interest within a patient using CW Doppler imaging, the switch 521 may be actuated to establish communication with the conductor 522 and the signal path 564 as shown in FIG. 5. In other words, the switch may establish communication between circuitry 520a and circuitry 520b when the system 100 performs CW Doppler imaging. While performing CW Doppler imaging, the ultrasound imaging system 100 may use the transmitting set 112b of transducer elements to transmit acoustic waves as illustrated by the arrow 552. In such a configuration, without the presence of the switches 521 or the conductors 522, the ADCs 220b are unused. The switches 521 may effectively combine the signal paths 564 with the signal paths 554 after the preamplifiers 219. For example, the switches 521 put the ADCs 220a and 220b in parallel such that a signal received by the receiving set 112a may be converted from digital to analog using both the ADCs 220a and the ADCs 220b. This combining of signal paths increases the dynamic range of the ADCs by at least 3 dB. Additional switches and conductors similar to the switches 521 and conductors 522 may be present within the probe 510 and/or the host 130 so as to recombine signal paths.

In some embodiments, the circuitry 520 acts on the analog signals from the receiving portion of the array 112a to limit slew rate. Functionally, the circuity to limit the slew rate can be an op-amp that clips against the power rails (e.g., power signal line 294) followed by an active low pass filter. This circuitry (and/or other circuitry of the block 520) can be integrated within the probe 510 as an integrated circuit.

Figure 6:
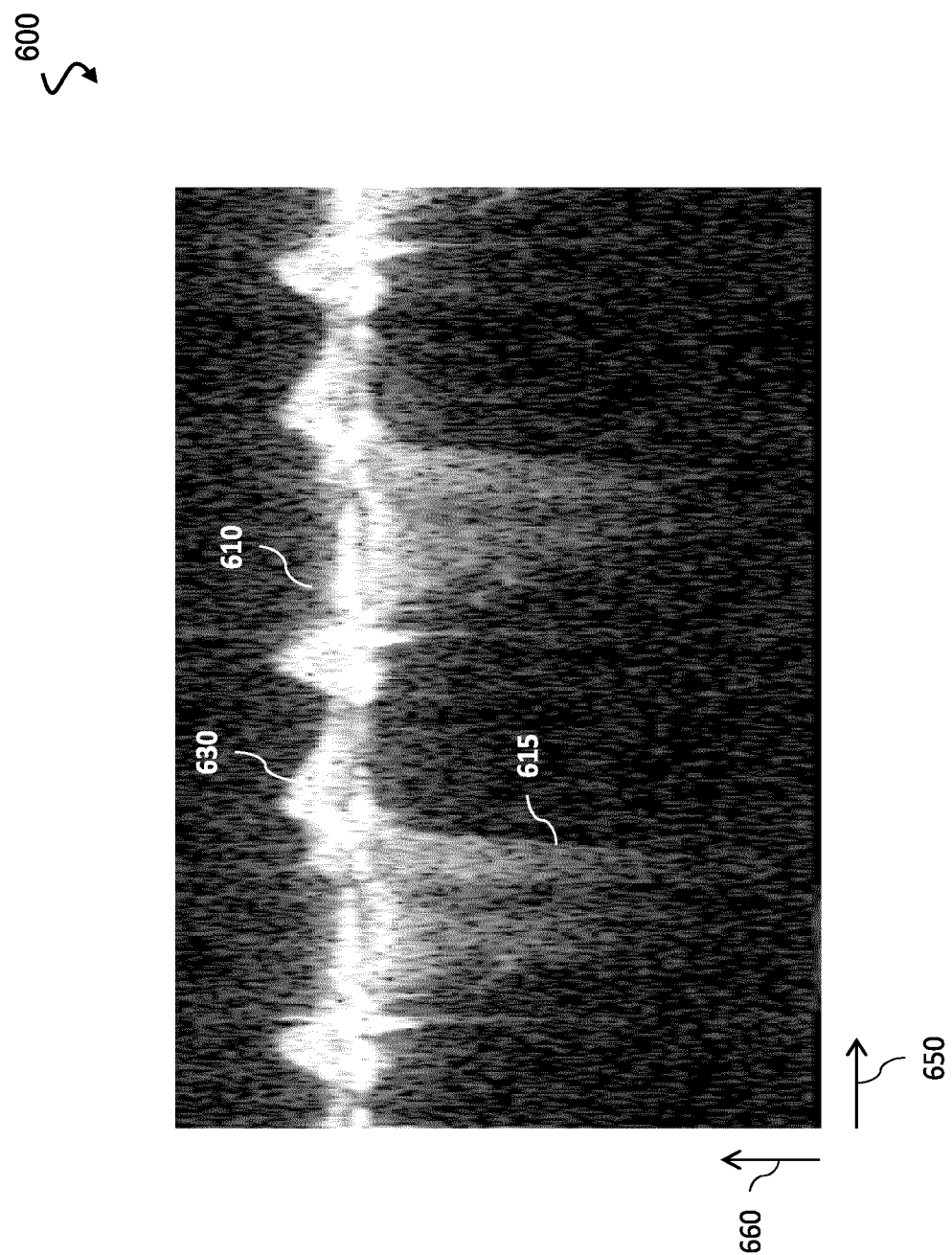
FIG. 6 is a graphical representation of a CW Doppler spectrum measured with an ultrasound imaging system, according to aspects of the present disclosure.

FIG. 6 is a graphical representation of a Doppler spectrum measured with an ultrasound imaging system, according to aspects of the present disclosure. The display 266 (FIG. 2) may display to a user a Doppler spectrum similar to the Doppler spectrum 600. Specifically, the Doppler spectrum 600 may be a depiction of data measured and processed using an ultrasound imaging system 100 with a probe similar to the probe 510 (FIG. 5) including the limiters 511, low pass filters 512, switches 521, and conductors 522. As a result, while the Doppler spectrum 600 is similar to the Doppler spectrum 400 (FIG. 4), the Doppler spectrum 600 also has differences. Specifically, the Doppler spectrum 600 may depict velocities of fluids and other objects but may include less sampling errors 420 due to increased dynamic range. Like the graphical representation of FIG. 4, an axis in direction 650 along the Doppler spectrum 600 may indicate a time dimension. A direction 660 along Doppler spectrum 600 may indicate a velocity, which may correspond to the velocity of blood within the heart or a blood vessel of a patient. In some embodiments, the Doppler spectrum velocity may correspond to blood flow through a mitral valve within a heart. The values 610 depicted within the Doppler spectrum 600 may indicate the velocity of a fluid at a given location within a patient at a given time. The Doppler spectrum 600 may differ from the Doppler spectrum 400, however, in that the Doppler spectrum 600 may include no or fewer sampling errors 420 of FIG. 4. Sampling errors 420 may be significantly reduced or not present within the Doppler spectrum 600 in part due to effect that the limiters 511 and low pass filters 512 have on decreasing the dynamic range of received signals. Additionally, the Doppler spectrum 600 may not include, or include less, sampling errors 420 as a result of the switches 521 and conductors 522 increasing the overall dynamic range of the ADCs within the probe 510.

Similar to the Doppler spectrum 400, the Doppler spectrum 600 may be presented or depicted to a user in any suitable format. For example, the display 266 may additionally display multiple metrics associated with the Doppler spectrum 600 or corresponding to the anatomy of the patient.

The Doppler spectrum 600 of FIG. 6 additionally includes a number of regions 615. The regions 615 may correspond to high velocities recorded and displayed to a user. These high velocities may correspond to leakage of various valves within a heart of a patient, or in any other suitable location within a vasculature of a patient. For example, a mitral valve within a patient's heart may not close completely and may leak, resulting in very high velocity jets of blood through a mitral valve when the valve is supposed to be closed while the heart pumps. The present invention is thus useful in diagnosing this or similar conditions within the heart or vasculature of a patient.

Figure 7:
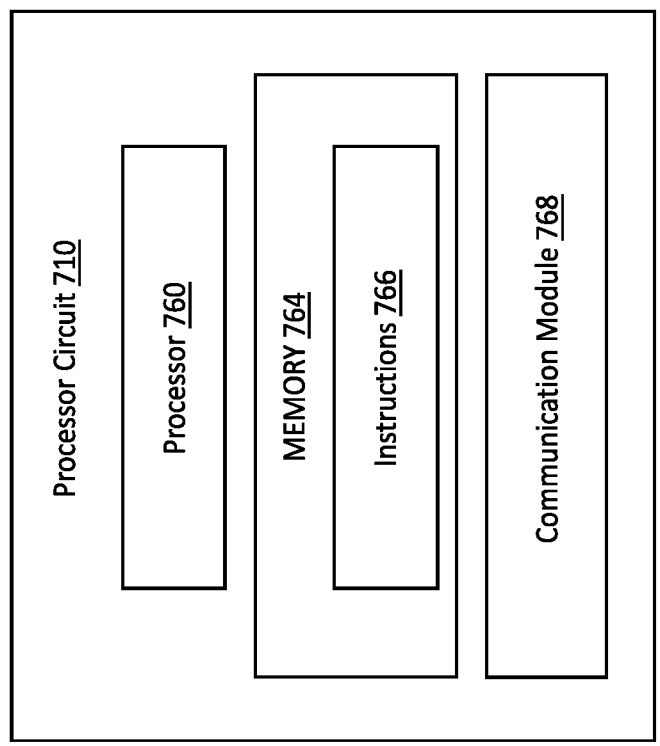
FIG. 7 is a schematic diagram of a processor circuit, according to aspects of the present disclosure.

FIG. 7 is a schematic diagram of a processor circuit, according to aspects of the present disclosure. The processor circuit 710 may be implemented in the host 130, probe 110 of FIG. 1, or in any other suitable location. One or processor circuits 710 can be configured to perform the operations described herein. The processor circuit 710 can include additional circuitry or electronic components, such as those described herein. In an example, the processor circuit 710 may be in communication with the transducer array 112 in the probe 110, circuitry 114, the communication interface 122, the communication interface 140, circuitry 134, and/or the display 132, as well as any other suitable component or circuit within the ultrasound system 100 (FIG. 1). As shown, the processor circuit 710 may include a processor 760, a memory 764, and a communication module 768. These elements may be in direct or indirect communication with each other, for example via one or more buses.

The processor 760 may include a CPU, a GPU, a DSP, an application-specific integrated circuit (ASIC), a controller, an FPGA, another hardware device, a firmware device, or any combination thereof configured to perform the operations described herein. The processor 760 may also be implemented as a combination of computing devices, e.g., a combination of a DSP and a microprocessor, a plurality of microprocessors, one or more microprocessors in conjunction with a DSP core, or any other such configuration.

The memory 764 may include a cache memory (e.g., a cache memory of the processor 760), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 764 includes a non-transitory computer-readable medium. The memory 764 may store instructions 766. The instructions 766 may include instructions that, when executed by the processor 760, cause the processor 760 to perform the operations described herein with reference to the probe 110 and/or the host 130 (FIG. 1). Instructions 766 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 768 can include any electronic circuitry and/or logic circuitry to facilitate direct or indirect communication of data between the processor circuit 710, the probe 110, and/or the display. In that regard, the communication module 768 can be an input/output (I/O) device. In some instances, the communication module 768 facilitates direct or indirect communication between various elements of the processor circuit 710 and/or the probe 110 (FIG. 1) and/or the host 130 (FIG. 1).

FIG. 8 is a flow diagram of a ultrasound imaging method 800, according to aspects of the present disclosure. One or more steps of the method 800 can be performed by a processor circuit of the ultrasound imaging system 100, including, e.g., the processor 760 (FIG. 7). As illustrated, method 800 includes a number of enumerated steps, but embodiments of method 800 may include additional steps before, after, or in between the enumerated steps. In some embodiments, one or more of the enumerated steps may be omitted, performed in a different order, or performed concurrently. The steps of method 800 can be carried out by any suitable component within ultrasound imaging system 100 and all steps need not be carried out by the same component.

At step 805, the method 800 includes generating analog ultrasound signals. Command signals may be generated at the host 130 and transmitted to the probe 110 via the signal line 292. The pulsers 218 may consequently generate a signal to excite the transmitting set 112b of transducer elements to generate ultrasound waves (FIG. 5). The transducers of the receiving set 112a may then receive echo signals reflected from features in the patient's anatomy and generate analog electrical signals representative of the ultrasound echoes. The generated analog ultrasound signals may then be transmitted to the circuitry 520a (FIG. 5).

At step 810, the method 800 includes limiting the slew rate of the analog signals so as to not over drive the analog to digital convertor, eliminating artifacts associated with motion and jitter. In some embodiments, the slew rate of the analog signals may be limited within the probe to match or not exceed the slew rate that can be handled by ADC 220 (FIG. 5) or any other component within the probe 510 or the system 100 such that artifacts in the graphical representations of blood flow velocities over cardiac cycles are advantageously avoided.

At step 815, the method 800 includes converting analog ultrasound signals to digital ultrasound signals. As shown previously, reflected ultrasound energy may be optionally reduced via the analog beamformer 214. Analog signals corresponding to reflected waves may then be transmitted to the ADCs 220, 220a, or 220b to be converted from analog ultrasound signals to digital ultrasound signals. Digital signals may then be further beamformed, multiplexed, or otherwise combined via the combiner 222 of FIG. 2, or any other suitable component before being transmitted to the host 130 via the cable 290. In some embodiments, digital ultrasound signals may be beamformed and/or otherwise combined via the combiner 222 located within the host 130 as shown in FIG. 3.

At step 820, the method 800 includes generating digital CW Doppler signals based on the digital ultrasound signals. CW Doppler signals may be generated via any suitable method based on the received digital ultrasound waves. For example, digital I/Q mixers can receive the digital ultrasound signals and generate the digital CW Doppler signals within the host 130.

At step 825, the method 800 includes processing the digital CW Doppler signals. Processing of the digital CW Doppler signals may include any suitable data processing component or procedure, including filtering via low pass filters, high pass filters or any suitable type of filter. Data processing may additional include windowing, summations, averaging, smoothing, transformations from one domain to another, such as fast Fourier transforms, and any other suitable conditioning to improve the overall data quality, clarity, or presentation. In addition, digital signal processing may be done via a processor, in software form, or with hardware, such as with physical circuitry within the host 130 or via any other suitable method or form.

At step 830, the method 800 includes generating graphical representations of blood flow velocities over cardiac cycles. The graphical representations may include any suitable means of data presentation. For example, graphical representations may include lists of data including time, velocities, dimensions, or data relating to the location of an imaged object within a patient's anatomy. Graphical representations may additionally include a Doppler spectrum similar to those depicted in FIG. 4 and/or FIG. 6. The graphical representations may also include any suitable plots, pictures, or depictions which may convey to a user information regarding the health or physical state of a patient. The graphical representations may also include any of the previously mentioned metrics relating to a patient's anatomy or a CW Doppler graph.

At step 835, the method 800 includes outputting the graphical representations of blood flow velocities over cardiac cycles to a display. Any of the previously mentioned graphical representations may be output to a display 132. Such graphical representations may be displayed in real time, as a sonographer conducts an ultrasound examination, or may be displayed at a later time. The graphical representations generated by the ultrasound imaging system 100 may be stored in the memory 764 in connection with the processor circuit 710 or may be stored on a cloud-based server or similar device. Any suitable metric associated with a patient's health or physical state either based on data collected with the ultrasound imaging system 100 or otherwise obtained with other equipment or procedures or from various different examinations at different times may also be displayed to a user accompanying any graphical representations.

Figure 9A:
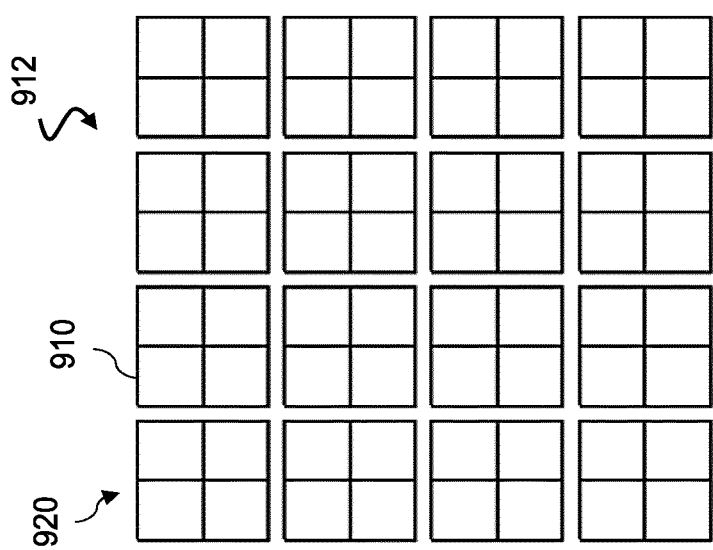
FIG. 9A is a schematic diagram illustrating an example ultrasound transducer array, according to aspects of the present disclosure.

FIG. 9A is a schematic diagram illustrating an example ultrasound transducer array 912, according to aspects of the present disclosure. The ultrasound transducer array 912 includes multiple ultrasound transducers 910 arranged into sub-arrays 920.

The transducer array 912 shown in FIG. 9A may be a 1.X-dimensional or two-dimensional matrix of ultrasound elements 910. The transducer array 912 may be substantially similar to the transducer array 112 of FIG. 1 and/or FIG. 2. In other embodiments, the transducer array 912 may also be a 1-dimensional linear array, or any other suitable type of array. As previously mentioned in regards to the transducer array 112, the transducer array 912 may include any suitable number of transducer elements 910. The transducer elements 910 may be arranged within transducer array 912 in multiple sub-arrays 920. The sub-arrays 920 may additionally be referred to as groups or patches, among other suitable terms. Each sub-array 920 may include four transducer elements 910, or any other suitable number of transducer elements 910. For example, the sub-array 920 may comprise 2, 4, 6, 8, 10, 12, or more transducer elements 910 as well as any suitable number therebetween. In addition, in some embodiments, each sub-array 920 need not include the same number of transducer elements 910, but each could vary according to any suitable arrangement or pattern. It is noted that the spacing between sub-arrays 920 shown in FIG. 9A does not necessarily indicate physical spacing or separation within the array. For example, each of the transducer elements in the array can have the same space with each adjacent element (whether or not that element is part of the same sub-array). Rather, the spacing shown in FIG. 9A can be illustrative of the sub-array groupings.

Figure 9B:
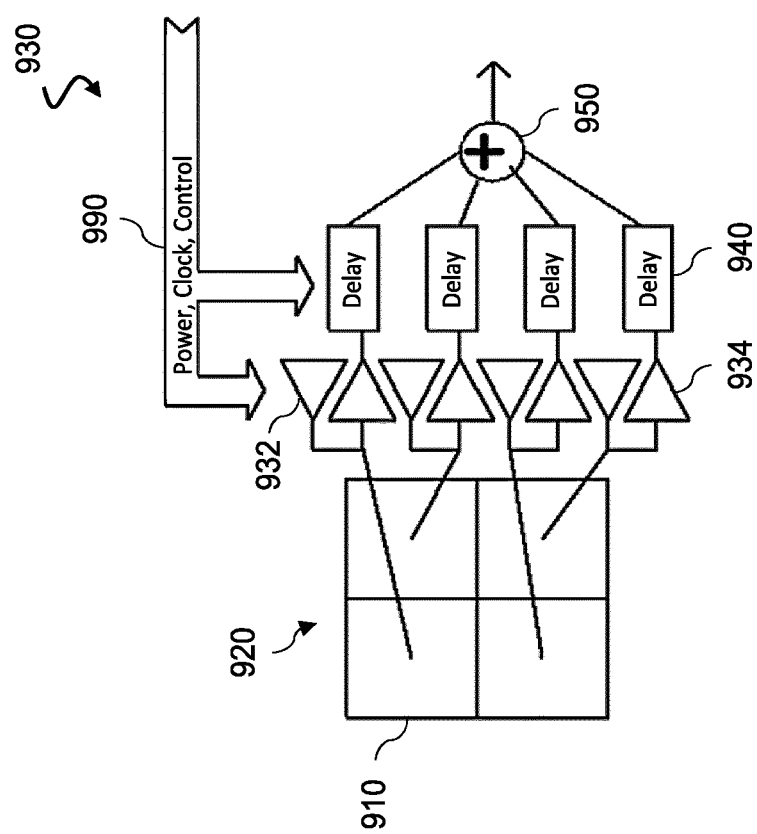
FIG. 9B is a schematic diagram illustrating example circuitry of an analog beamformer, according to aspects of the present disclosure.

FIG. 9B is a schematic diagram illustrating example circuitry of an analog beamformer 930, according to aspects of the present disclosure. The analog beamformer 930 may be substantially similar to the analog beamformer 214 of FIG. 2. FIG. 9B provides a more detailed view of the analog beamformer 930, which may be implemented within the ultrasound probe. The analog beamformer 930 includes multiple transmit pulsers 932, preamplifiers 934, delay circuits 940, a summation component 950, and conductors 990 providing power, clock, and/or control signals to any of these components. FIG. 9B additionally depicts one sub-array 920 including multiple ultrasound transducer elements 910. The sub-array 920 shown in FIG. 9B may be one of the sub-arrays 920 shown in FIG. 9A or may be a different sub-array.

The transmit pulsers 932 may be substantially similar to the pulsers 218 of FIG. 2. Specifically, the transmit pulsers 932 may receive command signals from the host and in response to these command signals, transmit high-voltage pulses to activate the ultrasound elements 910 to emit ultrasound energy that propagates into a patient's anatomy. Each ultrasound element 910 may therefore correspond to and/or be in communication with a transmit pulser 932.

Multiple preamplifiers 934 are additionally depicted in FIG. 9B. The preamplifiers 934 may be substantially similar to the preamplifiers 219 of FIG. 2. The preamplifiers 934 may amplify signals received from the ultrasound elements 910 to improve the quality of received signals by, for example, reducing a noise floor.

Multiple delay circuits 940 may be in communication with the preamplifiers 934 within the analog beamformer 930. The delay circuits 940 may be of any suitable type. For example, the delay circuits 940 may include analog delay circuitry for the analog beamformer 930. The delay circuits 940 may apply a delay profile to signals received from the ultrasound transducers 910 so as to perform beamforming in relation to all elements within a sub-array 920 or partial beamforming. Such delay profiles may be provided to the delay circuits 940 via any suitable method. For example, in some embodiments, a conductor corresponding to control or clock data within the conductors 990 may be in communication with the delay circuits 940 and may dictate delay profiles for the delay circuits 940.

FIG. 9B additionally depicts a summation component 950. The summation component 950 may be an analog adder circuit, summing mixer, or any suitable electronic component for summing signals. The summation component 950 is in communication with the respective outputs of the delay circuits 940. In such a configuration, the signals output from each delay circuit 940 may be summed in an analog fashion. In other embodiments, the summation component 950 may comprise any suitable circuitry or configuration to otherwise combine signals from the outputs of the delay circuits 940. The output of the summation component 950 may then be in communication with one or more T/R switches 216 from FIG. 2 and the signals combined by the analog beamformer 930 may be further processed and/or combined within the probe 110 and/or the host 130 as has been described or in any other suitable way.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound system, comprising:
a transducer array comprising:
   a first acoustic element configured to generate analog electrical signals; and
   a second acoustic element;
a first analog-to-digital converter (ADC) associated with the first acoustic element and configured to:
   receive the analog electrical signals generated by the first acoustic element; and
   convert the analog electrical signals to first digital electrical signals;
a second ADC associated with the second acoustic element;
a switch configured to establish communication between the second ADC and the first acoustic element such that the second ADC is configured to:
   receive the same analog electrical signals generated by the first acoustic element; and
   convert the same analog electrical signals to second digital electrical signals; and
a processor circuit in communication with the first ADC and the second ADC, wherein the processor circuit comprises digital in-phase/quadrature (I/Q) mixers configured to generate digital continuous wave (CW) Doppler signals based on the first and second digital electrical signals, and wherein the processor circuit is configured to:
   process the digital CW Doppler signals;
   generate a graphical representation of a distribution of blood flow velocities; and
   output the graphical representation to a display in communication with the processor circuit.

2. The system of claim 1, further comprising:
analog gain compression circuitry communicatively disposed between the transducer array and the first ADC.

3. The system of claim 1,
wherein the switch is configured to establish communication between the second ADC and the first acoustic element when the second acoustic element is a transmit element and the first acoustic element is a receive element.

4. The system of claim 1, wherein the processor circuit further comprises:
a digital low pass filter communicatively disposed between the digital I/Q mixers and the display; and
a digital high pass filter communicatively disposed between the digital low pass filter and the display.

5. The system of claim 1, wherein the processor circuit is configured to:
process the first and second digital electrical signals;
generate an ultrasound image of a heart; and
output the ultrasound image to the display.

6. The system of claim 1, further comprising:
analog limiter circuitry communicatively disposed between the transducer array and the first ADC.

7. The system of claim 6, wherein the analog limiter circuitry comprises soft limiter circuitry.

8. The system of claim 6, further comprising:
a low pass filter communicatively disposed between the analog limiter circuitry and the first ADC.

9. The system of claim 1, further comprising:
an ultrasound probe comprising a housing and a cable configured to transmit the first and second digital electrical signals; and
a host system in communication with the ultrasound probe via the cable,
wherein the transducer array is coupled to the housing of the ultrasound probe,
wherein the first ADC is disposed within the housing, and
wherein the processor circuit is disposed within the host system.

10. The system of claim 9, further comprising:
a preamplifier positioned between the transducer array and the first ADC disposed within the housing of the ultrasound probe.

11. The system of claim 9, further comprising:
circuitry for combining first and second digital electrical signals.

12. The system of claim 11, wherein the circuitry for combining first and second digital electrical signals is positioned within the housing of the ultrasound probe.

13. The system of claim 11, wherein the circuitry for combining digital electrical signals is positioned within the host system.

14. A method, comprising:
generating, using a first acoustic element of a transducer array, analog electrical signals;
converting, using a first analog-to-digital converter (ADC) associated with the first acoustic element, the analog electrical signals to first digital electrical signals;
connecting, using a switch, a second ADC to the first acoustic element, wherein the second ADC is associated with a second acoustic element of the transducer array;
converting, using the second ADC, the same analog ultrasound signals from the first acoustic element to second digital electrical signals;
generating digital continuous wave (CW) Doppler signals based on the first and second digital electrical signals;
processing the digital CW Doppler signals;
generating a graphical representation of a distribution of blood flow velocities; and
outputting the graphical representation to a display in communication with the processor circuit.

* * * * *